United States Patent [19]

Heitel

[11] Patent Number: 5,315,887
[45] Date of Patent: May 31, 1994

[54] MULTIPORT EQUALIZATION PROBE

[75] Inventor: Robert G. Heitel, Laguna Beach, Calif.

[73] Assignee: Baxter Diagnostics Inc., Deerfield, Ill.

[21] Appl. No.: 756,735

[22] Filed: Sep. 9, 1991

Related U.S. Application Data

[63] Continuation-in-part of Ser. No. 376,714, Jul. 7, 1989, abandoned, which is a continuation-in-part of Ser. No. 210,695, Jun. 23, 1988, Pat. No. 4,951,512.

[51] Int. Cl.$^5$ .................................. G01N 1/14
[52] U.S. Cl. .................................. 73/864.11
[58] Field of Search ............... 73/864.01, 864.11, 864.21–864.25, 73/864.74, 864.86, 864.87; 422/100, 63–65, 67, 81; 606/30–34, 44; 138/111, 113, 115–117

[56] References Cited

U.S. PATENT DOCUMENTS

| | | | |
|---|---|---|---|
| 1,930,182 | 10/1933 | Richardson | 152/12 |
| 2,210,546 | 8/1940 | Hassler | 73/864.74 |
| 2,256,656 | 9/1941 | Swabacker | 128/214 |
| 2,503,147 | 4/1950 | Applezweig | 226/116 |
| 2,584,397 | 2/1952 | Pitman | 226/116 |
| 2,689,562 | 9/1954 | Adams et al. | 128/214 |
| 2,855,929 | 10/1958 | Hein, Jr. | 128/221 |
| 3,759,667 | 9/1973 | Bannister et al. | 73/864.24 |
| 3,799,086 | 3/1973 | Bannister et al. | 73/864 |
| 3,817,090 | 6/1974 | Michel | 73/81 |
| 3,872,730 | 3/1975 | Ringrose et al. | 73/864 |
| 3,900,289 | 8/1975 | Liston | 23/230 R |
| 3,991,627 | 11/1976 | Laird et al. | 73/423 R |
| 4,046,511 | 9/1977 | Stabile | 33/16 |
| 4,080,833 | 3/1978 | Huber | 73/423 |
| 4,106,701 | 8/1978 | Siefken | 239/271 |
| 4,120,662 | 10/1978 | Fosslien | 73/864 |
| 4,123,173 | 10/1978 | Bullock et al. | 356/246 |
| 4,143,658 | 3/1979 | Rambosek et al. | 128/184 |
| 4,166,094 | 8/1979 | Froehlich et al. | 422/64 |
| 4,180,071 | 12/1979 | Oiwa | 128/218 N |
| 4,203,443 | 5/1980 | Genese | 128/272.3 |
| 4,210,724 | 7/1980 | Sogi et al. | 435/292 |
| 4,215,690 | 8/1980 | Oreopoulos et al. | 128/221 |
| 4,235,840 | 11/1980 | Mendoza et al. | 422/64 |
| 4,298,570 | 11/1981 | Lillig et al. | 422/64 |
| 4,340,390 | 7/1982 | Collins et al. | 23/230 B |

(List continued on next page.)

FOREIGN PATENT DOCUMENTS

| | | |
|---|---|---|
| 0041378 | 12/1981 | European Pat. Off. . |
| 0042036 | 12/1981 | European Pat. Off. . |
| 0061317 | 9/1982 | European Pat. Off. . |
| 0275119 | 7/1988 | European Pat. Off. . |
| 0355823 | 2/1990 | European Pat. Off. . |
| 933710 | 9/1955 | Fed. Rep. of Germany ... 73/864.01 |
| 2600299 | 7/1976 | Fed. Rep. of Germany . |
| 89/04955 | 6/1989 | PCT Int'l Appl. . |
| 89/12829 | 12/1989 | PCT Int'l Appl. . |
| 4005 | of 1882 | United Kingdom ............... 138/115 |
| 2095403 | 9/1982 | United Kingdom . |
| 19248 | 9/1983 | United Kingdom ............... 138/115 |

OTHER PUBLICATIONS

Hansen, "A Groundwater Profiles Sampler", vol. 10, No. 2, Water Resources Research, Apr. 1974.

*How To Use the CleanTech System*, 4 page pamphlet from CleanTech, published Nov. 1988.

*Factors Influencing The Coring of Rubber Closures*, G. H. Hopkins, Oct. 15, 1958; Technical Report No. 9, 6 pages.

*Coring: The Unseen Menace*, Peter A. Charlebois, B.SC., (List continued on next page.)

U.S. PATENT DOCUMENTS

*Primary Examiner*—Robert Raevis
*Attorney, Agent, or Firm*—Mark J. Buonaiuto; Louise S. Pearson; Paul C. Flattery

[57] ABSTRACT

A multiport equalization probe or needle includes an elongate body with a first and second end. The probe includes two or more lumens and an inlet and outlet for each lumen. It is closed at the first end which has a sharpened, conical configuration. Conduits provide separate connections between the lumens and a pump assembly which removes material through the lumens.

6 Claims, 5 Drawing Sheets

U.S. PATENT DOCUMENTS

| | | | |
|---|---|---|---|
| 4,475,411 | 10/1984 | Wellerfors | 73/864.24 |
| 4,477,190 | 10/1984 | Liston et al. | 356/418 |
| 4,478,095 | 10/1984 | Bradley et al. | 73/864.21 |
| 4,478,958 | 10/1984 | Carlson et al. | 264/53 |
| 4,484,483 | 11/1984 | Riegger et al. | 73/846.23 |
| 4,528,159 | 7/1985 | Liston | 422/65 |
| 4,577,514 | 3/1986 | Bradley et al. | 73/863.01 |
| 4,595,562 | 6/1986 | Liston et al. | 422/65 |
| 4,635,665 | 1/1987 | Namba et al. | 422/63 |
| 4,647,432 | 3/1987 | Wakatake | 422/64 |
| 4,662,231 | 5/1987 | Schoorschmidt et al. | 73/864.23 X |
| 4,665,758 | 5/1987 | Schoorschmidt et al. | 73/864.23 X |
| 4,669,321 | 6/1987 | Meyer | 73/863.85 |
| 4,703,762 | 11/1987 | Rathbone et al. | 128/763 |
| 4,713,974 | 12/1987 | Stone | 73/864.21 |
| 4,721,137 | 1/1988 | Muller | 141/65 |
| 4,743,243 | 5/1988 | Vaillancourt | 604/166 |
| 4,756,201 | 7/1988 | Uffenheimer | 73/864.21 |
| 4,788,871 | 12/1988 | Nelson et al. | 73/866.5 |
| 4,791,821 | 12/1988 | Spencer | 73/864.74 |
| 5,060,529 | 10/1991 | Bals et al. | 73/864.74 |

OTHER PUBLICATIONS

M.D., Can. Anaea. Soc. J., vol. 13, No. 6, Nov. 1966, pp. 585–597.

*New Developments In Hypodermic Needles,* Brian E. Baldwin, Bulletin of the Parenteral Drug Assoc., Nov.–Dec., 1971, vol. 25, No. 6, pp. 275–278.

*Purchasing Digest/Needle Sharpness,* N. J. Menolasino, Ph.D. and H. H. Hetz, M.D.; 2 pages.

*The Mechanism of Aging of Elastomers: I. Modes of Degradation and Protective Measures,* George H. Hopkins and Frank M. Keim, Bulletin of the Parenteral Drug Association, Jul.–Aug., 1977, vol. 31, No. 4, pp. 201–210.

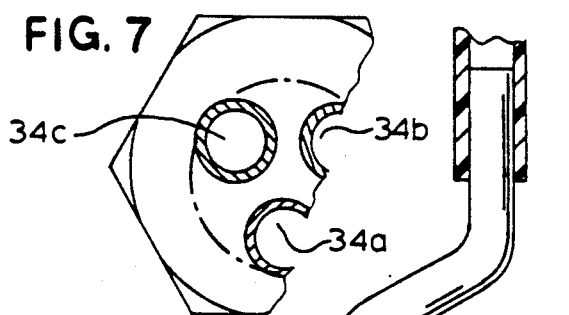
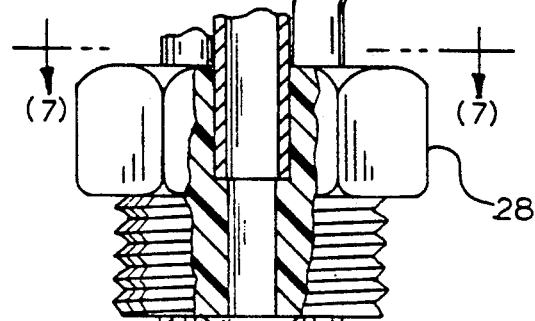
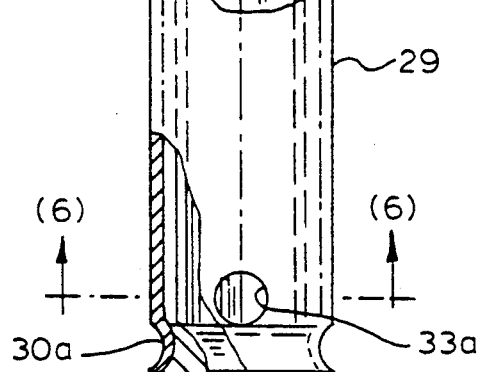
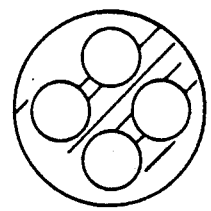
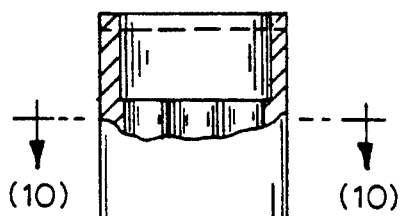
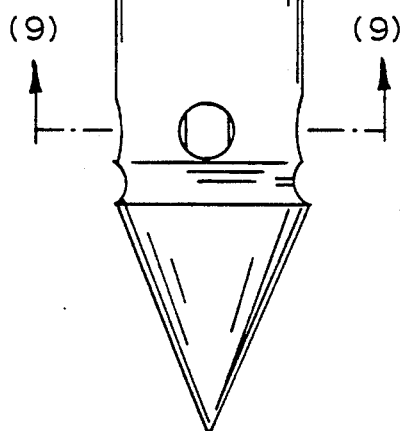
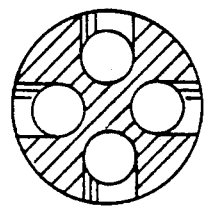

MULTIPORT EQUALIZATION PROBE

This application is a continuation-in-part of application Ser. No. 376,714, filed Jul. 7, 1989 for an "Assembly For Removing Waste From Closed Sample Containers" (now abandoned for file wrapper continuation application Ser. No. 655,248 filed Feb. 13, 1991, also abandoned for pending file wrapper continuation application Ser. No. 918,929 filed Jul. 22, 1992). Ser. No. 376,714 was a continuation-in-part of application Ser. No. 210,695, filed Jun. 23, 1988, for a "System For Providing Access To Sealed Containers", now U.S. Pat. No. 4,951,512.

BACKGROUND OF THE INVENTION

The present invention relates to a probe or needle for establishing communication with the inside of a closed sample container to remove fluid or debris from the container, and more particularly to a probe which defines two or more lumens and allows individual evacuation of each lumen.

In an automated system which uses a puncture tube to provide temporary access to a closed sample container through a stopper which closes the container, the puncture tube should not contact the sample or any contaminants adhered to the inside surface of the stopper. Such contact causes contamination of the puncture tube and ultimately cross-contamination of the samples which the system processes.

Thus, the system should include cleaning apparatus for removing excess sample and contaminants before the puncture tube extends into the container. This cleaning apparatus should include a penetrating component which can extend into the container through the stopper and quickly and effectively remove excess sample and/or debris from the bottom of the stopper and the surrounding area. The penetrating component, used in conjunction with a pumping system, should provide constant suction throughout this area to remove the contaminants.

The multiport equalization probe of the present invention used in conjunction with a pump assembly fulfills the requirements outlined above. It can easily move through a stopper and quickly and effectively remove excess sample and/or debris from the bottom of the stopper and the surrounding area by providing constant suction throughout this area.

SUMMARY OF THE INVENTION

In accordance with one embodiment of the present invention, a multiport equalization probe or needle includes an elongate body and a plurality of lumens. The probe body defines an inlet opening or port proximate a first end for each lumen. It has a sharpened, conical configuration at the first end so that it may easily move through a stopper of a closed container.

The process used to manufacture the probe of the present invention includes: forming an elongate body member defining a bore; forming a plurality of inlet openings in the body member proximate a first end of the bore; forming a fitting which defines a plurality of outlet openings; connecting the fitting with the body member to close the second end of the bore and to divide the bore into a plurality of lumens. Each lumen communicates with an inlet opening and an outlet opening. Alternatively, the process may include drilling or otherwise forming the lumens into a solid body member. It may also include injection molding the probe body.

A separate conduit connects each lumen with a pump which provides suction for removing material proximate the inlet or port of the lumen. This arrangement provides separate connection of each lumen to the pump's vacuum system, i.e., each lumen has its own vacuum chamber. Thus, the removal of material through one lumen does not affect the removal of material through another lumen.

BRIEF DESCRIPTION OF THE DRAWINGS

For a more complete understanding of this invention one should now refer to the embodiment illustrated in greater detail in the accompanying drawings and described below by way of an example of the invention. In the drawings:

FIG. 5 is a side elevation view of the multiport equalization probe of the present invention.

FIG. 6 is a cross-sectional view taken along line 6—6 in FIG. 5.

FIG. 7 is a cross-sectional view taken along line 7—7 in FIG. 5.

FIG. 8 is a side elevation view of a second embodiment of the multiport equalization probe of the present invention.

FIG. 9 is a cross-sectional view taken along line 9—9 in FIG. 8.

FIG. 10 is a cross-sectional view taken along line 10—10 in FIG. 10.

While the following disclosure describes the invention in connection with one embodiment and a modification, one should understand that the invention is not limited to this embodiment. Furthermore, one should understand that the drawings are not to scale and that graphic symbols, diagrammatic representations, and fragmentary views, in part, illustrate the embodiment. In certain instances, the disclosure may not include details which are not necessary for an understanding of the present invention such as conventional details of fabrication and assembly.

DETAILED DESCRIPTION OF THE DRAWINGS AND AN EMBODIMENT

Figure 1:
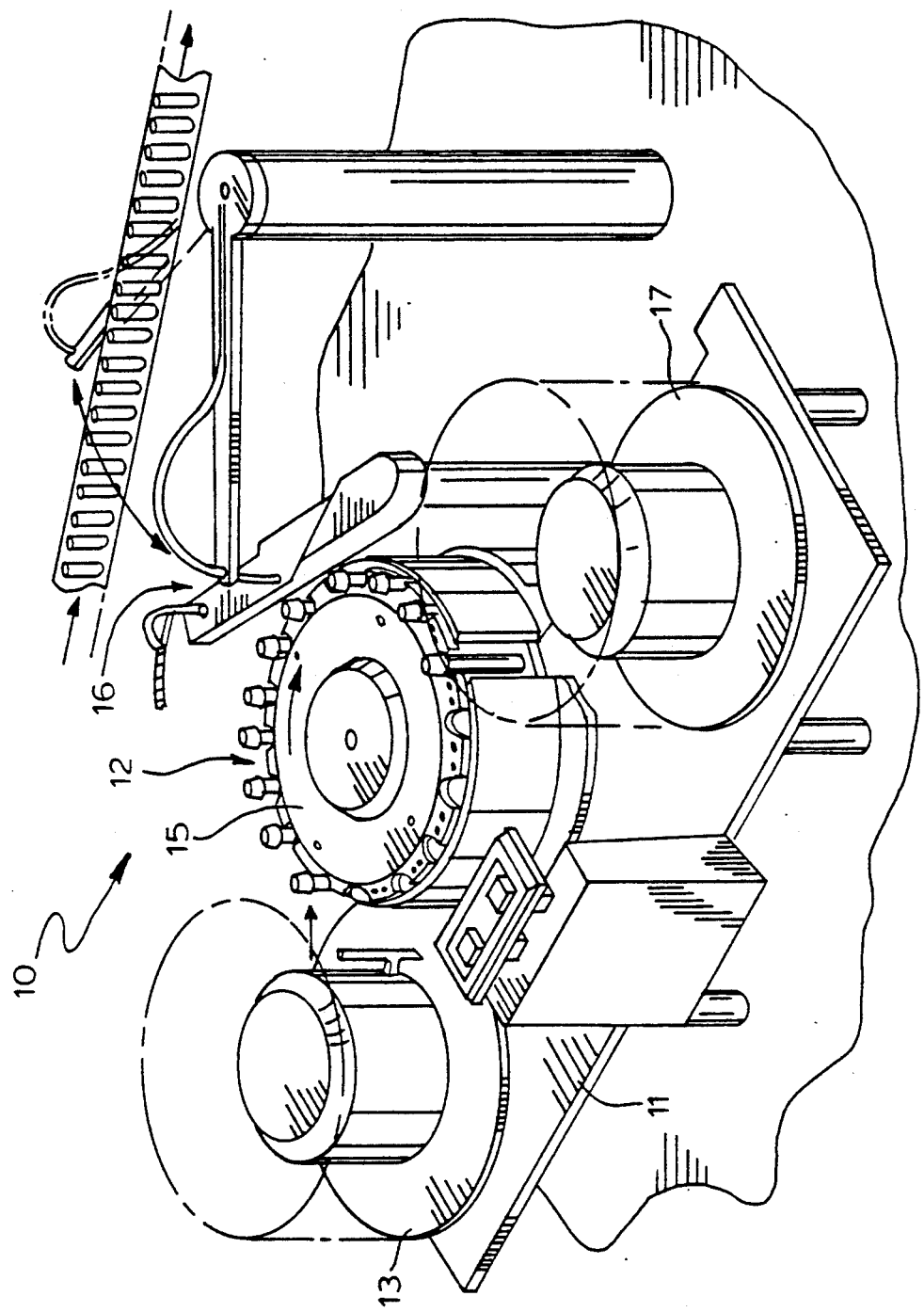
FIG. 1 is a perspective view of an automated sampling system which includes the waste removal assembly of the present invention. The aforementioned parent co-pending application Ser. No. 376,714 discloses the automated sampling system in greater detail; and the applicants incorporate that disclosure to the present disclosure by this reference.

Turning now to the drawings, FIG. 1 illustrates an automatic sampling system at 10. This system includes a base plate 11 for supporting a carousel assembly 12, including a loading carousel 13 which provides closed sample containers 14 to the system, a transfer carousel 15 which receives the sample containers 14 from the loading carousel 13 and moves them to a first location 16, and an unloading carousel 17 which receives the containers from the transfer carousel 15 and stores them for retrieval by an operator. The co-pending application Ser. No. 376,714, for an "Assembly For Removing Waste From Closed Sample Containers" discloses the automatic sampling system in greater detail. The applicants incorporate the disclosure of that application to the disclosure of the present application by this reference.

Figure 2:
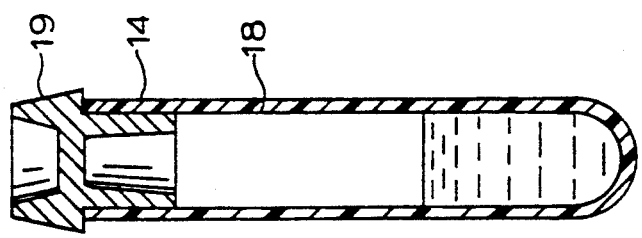
FIG. 2 is a sectional view of a sample container of a type used in the sampling system of FIG. 1.

The closed container 14, used with the system 10 and shown in FIG. 2, is preferably a glass tube 18 with an open top and a stopper 19 which normally closes the top opening. In addition, the stopper 19 is a self-sealing material, e.g., rubber, which can hermetically close a small slit or hole made in it by a slender puncture tube or needle. Alternatively, the system 10 may use containers of any suitable shape made of any suitable fluid-tight material. Also, the closure may be any suitable device with components which allow a penetrating member to displace them and define an opening through the closure, as described below.

Figure 3:
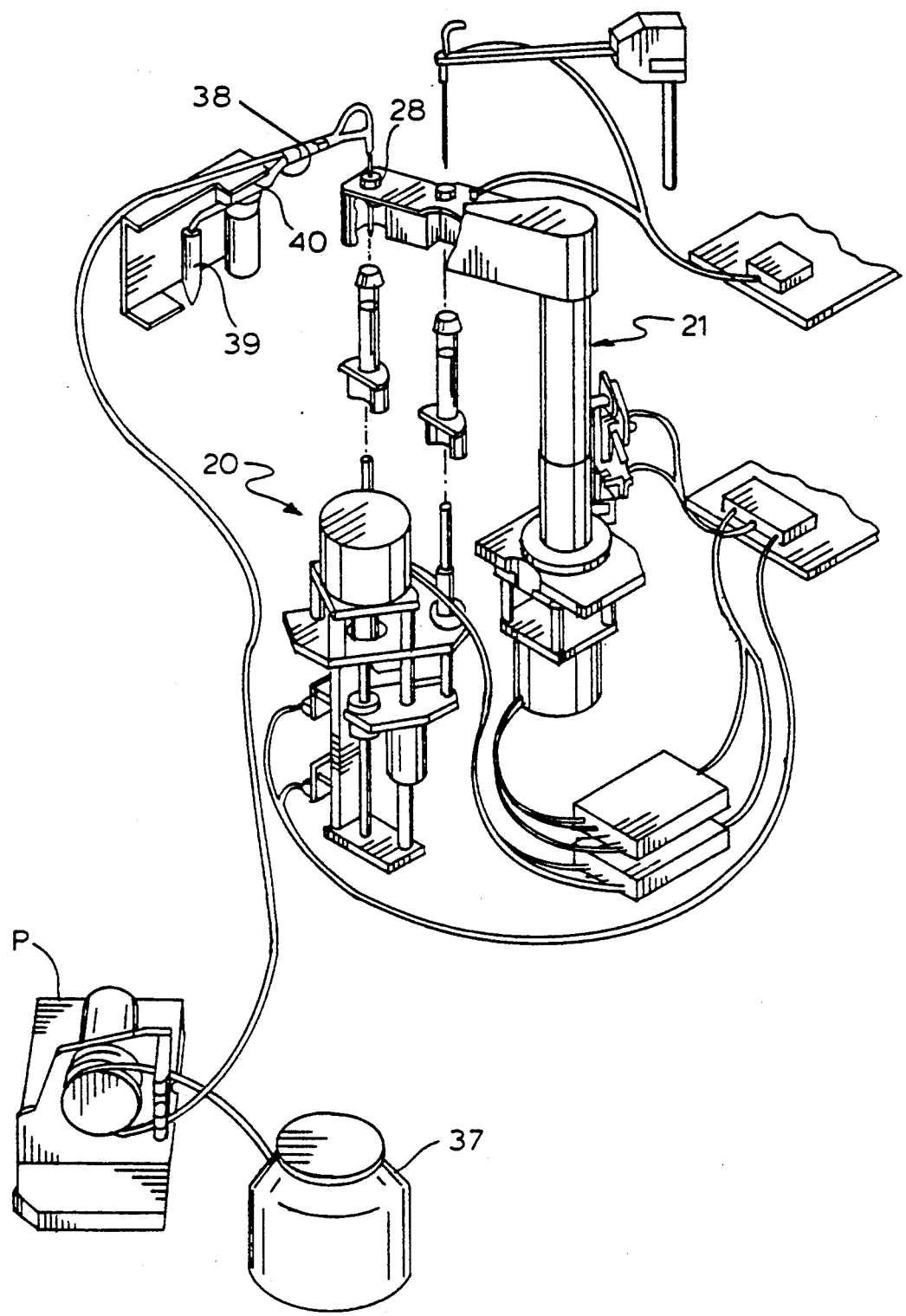
FIG. 3 is a schematic view of the waste removal assembly used in the automated sampling system of FIG. 1.

A lift mechanism 20 and a puncturing mechanism 21 (See FIG. 3), disposed at the first location 16, temporarily open the closure or stopper 19 of two consecutive or adjacent containers 14 placed there by the transfer carousel 15. The lift mechanism 20 drives two adjacent platforms of the carousel 15 disposed at the first location 16 and raises the containers 14 from a lowered position to a raised position. As the lifting mechanism 20 lifts the two containers 14, the puncturing mechanism 21 receives them and forms a temporary opening in the stoppers 19 of each container using the force provided by the lifting mechanism 20.

Figure 4:
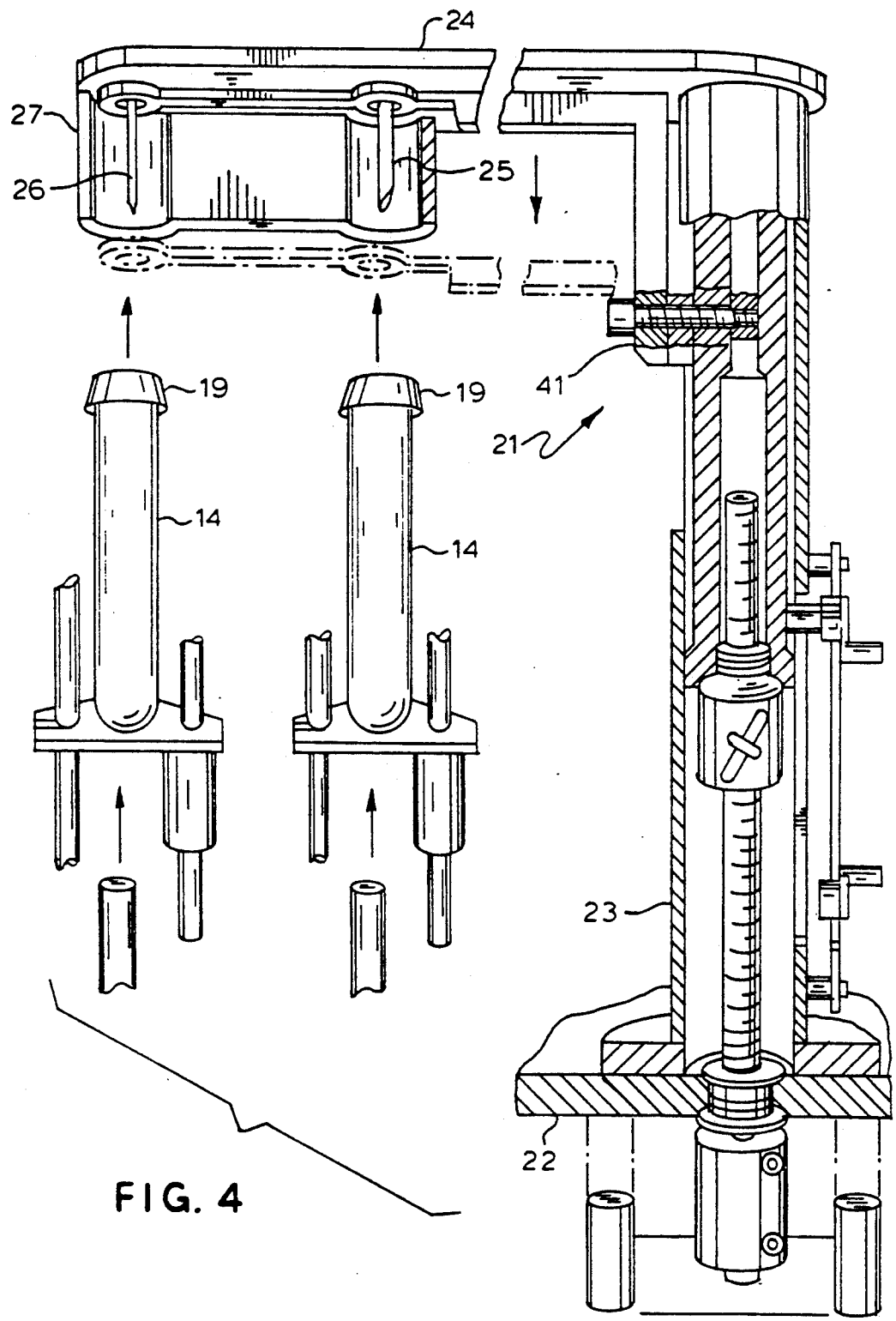
FIG. 4 is a side elevation view of the puncturing and stripper mechanisms used in the sampling system with portions broken away to expose their construction. This figure also includes two sample containers disposed below the needle and the hollow puncture tube.

Turning now to FIG. 4, the puncturing mechanism includes a securing plate 22 for attaching the mechanism 21 to the base plate 11 and a vertical support member 23 fixedly secured to the securing plate 22. The vertical member is a hollow tube made of metal or any other suitable material of high strength and rigidity. It supports a horizontal, cantilever member 24 fixedly secured to its top end. This horizontal support 24 supports a puncture tube 25 and the probe or cleaning needle 26 of the present invention in place at the first location 16.

The puncturing mechanism 21 also includes a transparent plastic shield 27 secured to the bottom of the member 24. This shield extends around the member 24 and downward of it. It shields the puncture tube 25 and the cleaning needle 26. Specifically, it receives the tops of containers 14 and prevents the operator from touching the sharp ends of the puncture tube 25 and the probe 26, protecting the operator from injury.

The probe 26 lies vertically and downwardly of the support member 24. It extends through an opening (not shown) in the member 24; and a fitting 28 (See FIGS. 3 and 5) removably secures the probe, with a threaded connection (or other similar connection), to the member 24. The probe 26 has an elongate body, including a tube 29 extruded or otherwise formed to a predetermined length of metal, e.g., stainless steel, or any other suitable material. The tube 29 defines a bore 29a which extends across its length.

A sharpened, generally conical head piece 30 extends into the bore 29a at a first end of the tube 29 to close the bore at that end. It defines a sharp distal end for the probe 26 which allows the probe to easily move through the stopper 19. The conical piece 30 includes a segment 30a which extends into the bore in pressure contact with the walls of the bore. Alternatively, a pinching of the tube 29 around the segment 30a (or a welding) may secure the conical piece 30 to the main body 29. In yet another alternative, the piece 30 and the tube 29 may be a one-piece integrally formed unit.

The fitting 28 closes the second, opposite end of the bore 29a. It is a one piece member, injection molded or otherwise formed of plastic or any other suitable material. It includes a segment 31 for extending into the bore 29a at the second end of the tube 29. This segment 31 has a generally Y-shaped cross-section; and its distal end engages the head piece 30. It includes three walls 31a, 31b, and 31c with outer side edges which extend longitudinally of the tube and engage the walls of the bore 29a, in pressure contact with them, to prevent rotation of the fitting 31 in the bore 29a.

The walls 31a–c and the walls of the bore 29a define three lumens 32a–c. Alternatively, the probe 26 may be a one-piece, integrally formed unit with two lumens, four lumens (as shown in FIGS. 8-9), or more than four lumens. In addition, the tube and head piece may be a one-piece integrally formed unit which defines two or more lumens and has a fitting which extends into one end of the unit to close the lumens but not to help define them (See the top of FIG. 8).

Three ports 33a, 33b and 33c formed into the tube 29 transversely of the tube 29 and proximate the end with the conical head piece 30 (the first end) serve as inlets for the lumens 32a–c, respectively. The three ports 33a–c lie 120° apart; and they establish communication between the probe 26 and the area around the entire periphery of the first end of the probe 26.

Three outlets 34a, 34b and 34c formed into the fitting 28 allow fluid communication between the lumens and three conduits 35a–c. Each outlet communicates with one of the three spaces between the walls 31a–c. One end of each of three stainless steel tubes 36a–c (or tubes made of any other suitable material) extends into a corresponding outlet in pressure contact with the walls of the outlet. The other end extends into a corresponding conduit (in pressure contact with the walls of the conduit) to connect the two together.

Figure 11:
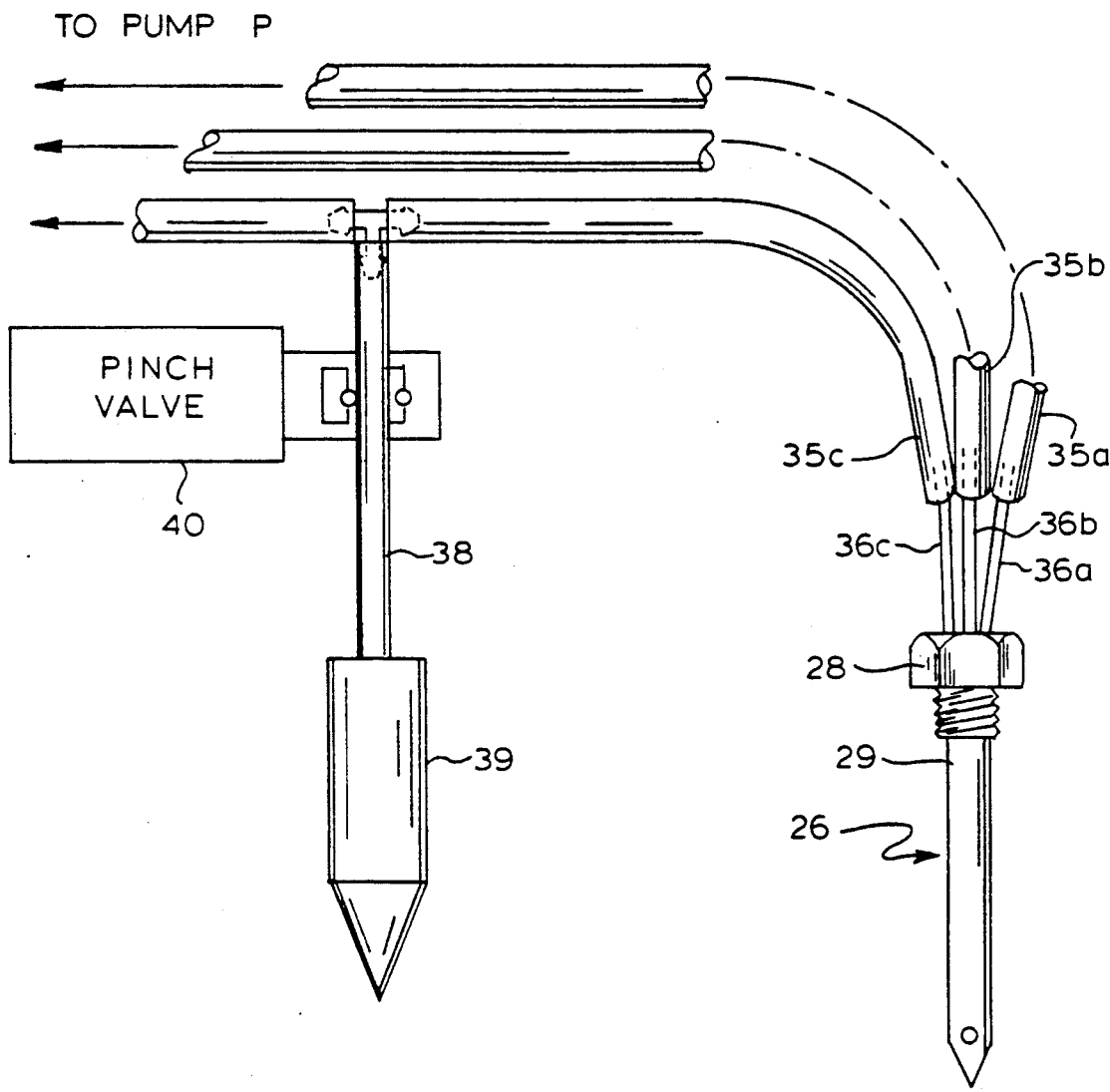
FIG. 11 is a side elevation view of the probe of the present invention and the conduits which connect it to a pump and a venting assembly.

The conduit 35a connects the lumen 32a to a pump P through the outlet 34a and the tube 36a. Similarly, the conduit 35b connects the lumen 32b to the pump P; and the conduit 35c connects the lumen 32c to the pump P (See FIG. 11). This arrangement provides separate connection of each lumen to the pump's vacuum system, i.e., each lumen has its own vacuum chamber. Thus, each lumen may remove the material proximate its inlet without any other lumen affecting its operation.

While the system 10 conducts sampling operations through the puncture tube 25, it cleans the stopper 19 and surrounding area of the adjacent tube 14 with the probe 26 (See FIG. 4). Tubing 35a–c connects the lumens 32a–c to the pump P (e.g. a peristaltic pump) which activates when the lift mechanism 20 begins to raise the containers 14. The pump P continues to operate until the electronic controls of the system 10 deactivate it, after a predetermined time period.

While it operates, the pump P manipulates, i.e., decreases, the pressure through the tubing 35a–c and the lumens 32a–c. Alternatively, the pump P may increase the pressure. It removes debris and/or sample, e.g., blood serum, entrapped on the inside surface of the stopper 19 or otherwise displaces this waste away from the inside surface of the stopper and the surrounding inside surface of the container 14.

The pump P moves this waste through the ports 33a-c in the probe 26, through the lumens 32a-c and the tubing 35a-c, and into a waste container 37 for disposal. (See FIG. 3) It performs this function by developing a negative pressure in the probe 26 and the tubing 35a-c. The negative pressure that it develops must have an intensity sufficient to remove the waste but not the sample disposed generally at the bottom of the container 14. Sealing each lumen from the other lumens is not necessary, as long as any opening between the lumens is substantially smaller than any of the port openings 33a-c.

After the pump P has stopped operating and drawing off waste, the system 10 vents the container 14 to atmosphere before withdrawing the probe 26. It does so through tubing 38 (See FIG. 11) which connects the tubing 35a with a waste container 39. A pinch valve 40 closes this tubing until the system controls open the pinch valve and the tubing. This venting provides a rapid flow of air through the tubing 35a and the lumen 32a, and into the container 14. The negative pressure developed by the pump P in the container 14 causes this flow as venting occurs. The flow may provide additional flushing of any remaining sample and/or debris from the bottom of the stopper and the surrounding area into the container 14.

Alternatively, the system may include means for venting through any one of the other conduits, a combination of two conduits, or all three conduits. In addition, the system 10 may include a pump or other similar device to enhance this venting operation.

After venting the container 14, the pinch valve remains open and closes again when the system moves the next container in position for waste removal or displacement. In emergency situations, when a positive pressure develops in the container 14 and the pinch valve does not close, the tubing receives any serum which flows out of the container 14 through the probe 26. This serum flows into the waste container 39 for disposal.

After removing waste from one container 14 and sampling an adjacent container 14, a stripper mechanism 41 (See FIG. 4) disposed in the vertical support 23 of the puncturing mechanism 21 strips the stoppers 19 from the puncture tube 25 and the probe 26 as the lift mechanism 20 lowers its plungers 20a and 20b. This mechanism 41 disengages the containers 14 from the puncturing mechanism 21 and allows them to move back into the compartments of the carousel 15.

While the above description and the drawings illustrate one embodiment and a modification, one should understand, of course, that the invention is not limited to this embodiment. Those skilled in the art to which the invention pertains may make modifications and other embodiments employing the principles of this invention particularly upon considering the foregoing teachings. The applicants, therefore, by the appended claims, intend to cover any modifications and other embodiments as incorporate those features which constitute the essential features of this invention.

What is claimed is:

1. In a sampling and cleaning apparatus with a pump assembly which includes a pump and a plurality of conduits through which the pump moves material, a cleaning needle for extending into a sealed container through a closure of the container to remove material from the container, said needle including an elongate body having a first and second end, a plurality of lumens in the body, an inlet opening for each lumen, said openings being disposed in a side of the body proximate the first end of the body, and an outlet opening proximate or at the second end of the body for each lumen, said elongate body being closed and sharpened at the first end, said pump assembly conduits being in communication with the lumen outlets, said pump assembly including a conduit for each lumen, each conduit connecting the corresponding lumen to the pump and combining with the corresponding lumen to define a vacuum chamber for removing a predetermined material.

2. The cleaning needle of claim 1, wherein the elongate body has a generally cylindrical configuration.

3. The cleaning needle of claim 2, wherein the inlet openings are spaced apart substantially equal distances around the sides of the elongate body.

4. The cleaning needle of claim 3, wherein the elongate body includes an elongate tube and a sharpened head piece at the first end.

5. The cleaning needle of claim 4, wherein the sharpened first end has a conical configuration.

6. In a sampling and cleaning apparatus, a cleaning needle extending into a sealed container through a closure of the container, said needle comprising: an elongate tube defining a bore; a sharpened head piece member secured to one end of the tube, said head piece member closing a first end of the bore; a fitting member secured to said tube at the second end of the bore, said fitting member extending into the bore and cooperating with the tube to define a plurality of elongate lumens; said tube defining an inlet opening for each lumen; said fitting member defining an outlet opening for each lumen.

* * * * *